United States Patent [19]

Minchin et al.

[11] Patent Number: 5,538,956
[45] Date of Patent: Jul. 23, 1996

[54] AMINE DERIVATIVES CONTAINING A PHOSPHONIC ACID MOIETY

[75] Inventors: Michael C. Minchin, Oxford; John F. White, Wokingham, both of England

[73] Assignee: John Wyeth & Brother, Limited, Maidenhead, England

[21] Appl. No.: 244,525

[22] PCT Filed: Dec. 1, 1992

[86] PCT No.: PCT/GB92/02229

§ 371 Date: Jun. 1, 1994

§ 102(e) Date: Jun. 1, 1994

[87] PCT Pub. No.: WO93/11138

PCT Pub. Date: Jun. 10, 1993

[30] Foreign Application Priority Data

Dec. 2, 1991 [GB] United Kingdom ............. 9125615

[51] Int. Cl.⁶ ............. A61K 31/66; C07F 9/38; C07F 9/40
[52] U.S. Cl. ............. 514/114; 558/166; 562/11
[58] Field of Search ............. 514/114; 558/166; 562/11

[56] References Cited

U.S. PATENT DOCUMENTS

| | | | |
|---|---|---|---|
| 3,812,221 | 5/1974 | Braden et al. | 562/11 X |
| 4,656,298 | 4/1987 | Dingwall et al. | 514/114 X |
| 5,190,934 | 3/1993 | Mickel et al. | 514/114 |
| 5,229,379 | 7/1993 | Marescaux et al. | 514/114 |
| 5,281,747 | 1/1994 | Hall et al. | 562/11 |

FOREIGN PATENT DOCUMENTS

| | | |
|---|---|---|
| 0181833 | 5/1986 | European Pat. Off. |
| 0319482 | 6/1989 | European Pat. Off. |
| 0345068 | 12/1989 | European Pat. Off. |
| 0407032 | 1/1991 | European Pat. Off. |
| 2104078 | 3/1983 | United Kingdom . |
| 0463560 | 1/1992 | United Kingdom . |

OTHER PUBLICATIONS

D. Brigot et al, Tetrahedron, vol. 35, No. 11, 1979 pp. 1345–1355.

Primary Examiner—Robert W. Ramsuer
Assistant Examiner—Michael G. Ambrose
Attorney, Agent, or Firm—Arthur G. Seifert

[57] ABSTRACT

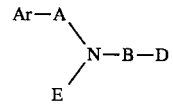

(I)

This invention concerns compounds of formula (I) wherein E represents hydrogen, $C_1$–$C_6$ alkyl or a group $Ar^1$-$A^1$; Ar and $Ar^1$ when present each represent an aryl group of 6 to 10 carbon atoms or a heteroaryl group of 5 to 10 ring atoms wherein the heteroatoms are selected from oxygen, nitrogen and sulphur, which may be optionally substituted by one or more substituents selected from alkyl of 1 to 6 carbon atoms, alkoxy of 1 to 6 carbon atoms, halogen, haloalkyl of 1 to 6 carbon atoms, haloalkoxy of 1 to 6 carbon atoms, cyano, amino, mono- or di-($C_1$–$C_6$) alkylamino, hydroxy and nitro; A and $A^1$ when present are the same or different alkylene groups having one or two carbons linking Ar or $Ar^1$ to N, each optionally substituted by alkyl of 1 to 6 carbon atoms or an optionally substituted Ar group as defined above, B is a straight chain alkylene group of 3 or 4 carbon atoms optionally substituted by alkyl of 1 to 6 carbon atoms, and D represents one of the following

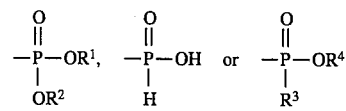

where $R^1$ and $R^2$ are independently hydrogen, alkyl of 1 to 6 carbon atoms or aralkyl of 7 to 12 carbon atoms; $R^3$ is —CH(Oalkyl)$_2$ in which the alkyl group contains 1 to 6 carbon atoms and $R^4$ is alkyl of 1 to 6 carbon atoms or aralkyl of 7 to 12 carbon atoms, which compounds are GABA autoreceptor agonists useful as antidepressants and for treating senile dementia.

13 Claims, No Drawings

AMINE DERIVATIVES CONTAINING A PHOSPHONIC ACID MOIETY

This application was filed under 35 U.S.C. § 371 and was based upon PCT International Application No. PCT/GB92/02229 which was filed on Dec. 1, 1992.

This invention relates to amines possessing a pharmacological activity, to processes for preparing them and to pharmaceutical compositions containing them. More particularly this invention relates to amines useful in the treatment of depression.

In the UK the annual referral rate for depression is around 300–400 per $10^5$ population of whom 10–15% require hospitalisation. At present the most effective and safe treatment for severe depression involves electroconvulsive therapy (ECT) where the patient receives a series of controlled electric shocks. However such treatment understandably engenders an atavistic fear and apprehension in many patients. It also has undesirable side-effects, notably disturbance of memory.

ECT is also expensive and time-consuming to administer, requiring the presence of specialist doctors such as psychiatrists and anaesthetists. As an alternative to ECT, drug therapy provides a more acceptable treatment for the patient but at the present time such therapy has not displaced ECT as the optimal treatment in severe cases because it is not always effective. There is therefore a need for new drugs for the treatment of depression, especially drugs having new modes of action mimicking ECT.

The mode of action of ECT remains unknown but in recent years much has been learnt about the biological effects of electroconvulsive shock (ECS) in animals. In particular, repeated ECS, given in ways closely mimicking those used to administer ECT clinically, elicits in rodents changes in monoamine functions. These include: increased 5-HT-mediated behaviour, increased dopaminergic behaviour and depressed beta-adrenoceptor binding and sensitivity of the coupled adenylate cyclase. The last is also seen following chronic treatment with a number of antidepressant drugs.

The effects of repeated ECS are presumably a response or adaptation to the acute effects of the seizures. Among these acute effects are a marked change in the release, synthesis and level of gamma aminobutyric acid (GABA) in the brain.—see Green A. R. et al, British J. Pharmacol., 92, 5–11 and 13–18 (1987) and Bowdler et al, ibid, 76, 291–298 (1982).

GABA is one of the most widespread and abundant transmitters in the mammaltan central nervous system and plays a major role in the control of brain excitability. It is similarly implicated in the benzodiazepine-mediated relief of anxiety. Recently, evidence has come to light which suggests that GABA transmission may also be involved in the therapeutic effects of some antidepressant treatments. In particular, new compounds designed as GABA agonists (e.g. fengabine and progabide) have been shown in preliminary clinical trials to have antidepressant activity (vide infra). Taken together, these findings suggest that interventions directed specifically at GABA transmission may provide the basis of novel therapies for the treatment of affective disorders.

At present three GABA receptors have been identified in the central nervous system. These are (1) a $GABA_A$-receptor known to be mainly postsynaptic and mediating inhibition of neuronal firing—see for example Stephenson, F. A. Biochem, J., 249 pp 21–32 (1988); (2) a $GABA_B$ receptor located both postsynaptically and presynaptically, where it mediates the inhibition of release of a number of neurotransmitters, e.g. noradrenaline and aspartic acid,—see for example Bowery, N. G. et al, Nature, 283, 92–94 (1980); and (3) a GABA autoreceptor which modulates the release of GABA from neurones—see for example Mitchell, P. R., and Martin, I. L. Nature, 274 904–905 (1978); Arbilla, S. Kanal, J. L and Langer, S. Z. Eur.J.Pharmac., 57, 211–217 (1979) and Brennan M. J. W. et al, Molec. Pharmac., 19, 27–30 (1981).

The pharmacological importance of these receptors is currently a subject of investigation with a major part of the work involving the search for anticonvulsant drugs with a mode of action involving $GABA_A$ receptors. Two drugs acting on GABA receptors, progabide and fengabine, have also been shown to possess antidepressant effects in preliminary clinical trials—see P. L. Morselli et al, L.E.R.S. Vol 4 (1986) pp 119–126 and B. Scatton et al, Journal of Pharm. and Exp. Therapeutics., 241, 251–257 (1987). The latter workers showed that fengabine possessed a biochemical mode of action different from that of conventional antidepressants but that the mechanism whereby fengabine exerted its antidepressant actions was not yet clear. It was thought to derive from a GABAergic action, most likely at $GABA_A$ receptors.

In the case of progabide, Morselli et al also attributed the antidepressant effect to an increased GABAergic transmission.

In copending UK patent publication No 2219295B evidence is provided that the antidepressant effect of progabide and fengabine is in fact due to their agonist action at the GABA autoreceptor.

The GABA autoreceptor is capable of regulating the release of GABA from GABAergic neurons which means an agonist at the autoreceptor would decrease the GABA release hence decreasing GABA function ie. an action opposite to that of $GABA_A$ agonists. Previously the autoreceptor was believed to have the same pharmacology as the $GABA_A$ site—see Molec. Pharm, 19, 27–30 (1981). We have found that the GABA autoreceptor has its own distinct pharmacology and that there are compounds having selective agonist activity at the GABA autoreceptor. These compounds have valuable medical uses.

There is also evidence that compounds acting at the benzodiazepine receptor as inverse agonists decrease GABA function in the brain and thus increase acetylcholine transmission. In addition, probably as a consequence of these actions, they facilitate memory in animals and man (see Sarter. M. et al. Trends in Neuroscience, 11 13–17, 1988). Compounds acting as GABA autoreceptor agonists are believed to have similar actions such as nootropic activity (e.g. increased vigilance and cognition) and are therefore useful in the treatment of cerebral insufficiency disorders and dementias.

Accordingly this invention provides a compound having formula:

or a salt thereof, wherein E represents hydrogen, lower alkyl or a group $Ar^1-A^1-$; Ar and $Ar^1$ are the same or different aryl groups (including heteroaryl) which are optionally substituted, e.g. by one or more substituents the same or different commonly used in pharmaceutical chemistry such as lower alkyr, lower alkoxy, halogen, haloweralkyl, halower-alkoxy, cyano, amino (including substituted amino eg.

mono- or di-loweralkyl amino), hydroxy and nitro; A and $A^1$ when present are independently an alkylene group having one or two carbon atoms linking Ar or $Ar^1$ to N, which group is optionally substituted by lower alkyl and/or optionally substituted aryl (including heteroaryl), B is a straight chain alkylene group of 3 or 4 carbon atoms, which may be substituted by lower alkyl; D represents —P(=O)(OR$^1$)(OR$^2$) where $R^1$ and $R^2$ are independently hydrogen, loweralkyl or $C_7$–$C_{12}$ aralkyl; —P(H)(=O)(OH) or —P(=O)($R^3$)(OR$^4$) where $R^3$ is CH(O alkyl)$_2$ and $R^4$ is loweralkyl or $C_7$–$C_{12}$ aralkyl.

By the term "lower" is meant a group containing 1 to 6 carbon atoms, preferably 1 to 4 carbon atoms. Examples of lower alkyl are methyl, ethyl, propyl and butyl.

Examples of $R^1$ and $R^2$ include hydrogen, methyl, ethyl, propyl and butyl and aralkyl groups of 7 to 12 carbon atoms e.g. benzyl, 2-phenethyl.

Examples of $R^3$ are CH(Oloweralkyl)$_2$ such as CH(OMe)$_2$, CH(OEt)$_2$ or CH(OPr)$_2$.

Examples of $R^4$ are methyl, ethyl, propyl and butyl and aralkyl groups of 7 to 12 carbon atoms e.g. benzyl or 2-phenethyl.

Examples of Ar and $Ar^1$ are mono- or bi-cyctic aryl groups such as carbocyclic aryl groups of 6 to 10 carbon atoms (e.g. phenyl or naphthyl) and mono- or bi-cyclic heteroaryl groups of 5 to 10 fine atoms in which the heteroatom is selected from oxygen, nitrogen and sulphur (e.g. furan, pyridine, thioohene) or aromatic groups containing two or more such heteroatoms (e.g. thiazolyl). Bicyclic heteroaryl groups are exemplified by quinoline (e.g. quinol-6-yl, quinol-2-yl) and benzofuran (e.g. benzofuran-2-yl).

Examples of A and $A^1$ are independently —(CH$_2$)$_m$— optionally substituted by lower alkyl and/or aryl where m is 1 or 2. Preferably A and $A^1$ are independently —CHR$^8$— where $R^8$ is hydrogen, lower alkyl, eg. methyl or ethyl, or optionally substituted aryl or heteroaryl as defined for Ar, e.g. phenyl. Examples of B are —CH$_2$CH$_2$CH$_2$— and such a group substituted by lower alkyl such as methyl, e.g. B represents —CH(CH$_3$)CH$_2$CH$_2$— or —CH$_2$CH(CH$_3$)CH$_2$—.

Examples of substituents on Ar, $Ar^1$ and $R^8$ when aryl or heteroaryl are one or more of the following methyl, ethyl, propyl, butyl, methoxy, ethoxy, n-propoxy, n-butoxy, fluorine, chlorine, bromine, chloromethyl, chloroethyl, trifluoromethyl, trifluromethoxy, cyano, amino, methylamino, ethylamino, n-propylamino, hydroxy, dimethylamino, diethylamino, methylethylamino and nitro.

The compounds of formula I as defined above possess pharmacological activity especially activity affecting the nervous system. In particular the compounds of formula I are inhibitors of gamma aminobutyric acid (GABA) release from nerve terminals via action on the GABA autoreceptor.

The compounds of formula I demonstrate activity at GABA autoreceptors more specifically they demonstrate agonist activity as shown by standard in vitro test procedures. The following test procedures were used to measure activity at (a) GABA autoreceptors and GABA$_B$ receptors by inhibition of potassium-evoked GABA and noradrenalin release from rat cortex in vitro (Procedure 1):

Procedure (1)

Slices (0.25×0.25×2.0 mm) of rat cerebral cortex are prepared using a McI]wain tissue chopper. The slices are incubated in Krebs-Henseleit solution containing [$^3$H]-GABA (10$^{-7}$M) and [$^{14}$C]-noradrenaline (10$^{-7}$M) in the presence of amino-oxyacetic acid (AOAA) (10$^{-5}$M), pargyline (10$^{-6}$M) and ascorbic acid (10$^{-4}$M), for 20 minutes at 37° C., rinsed with 5 ml aliquots of Krebs-Henseleit solution and transferred to 10 superfusion chambers (volume 300 µl). The slices are continuously superfused with Krebs-Henseleit solution (0.4 ml min$^{-1}$) containing AOAA (10$^{-5}$M) and fractions of the superfusate collected every 4 minutes. Transmitter release is induced by 4 minute exposure to a Krebs-Henseleit solution containing 25 mM potassium (with concomitant reduction in sodium to maintain osmolarity) after 68 ($S_1$) and 92 ($S_2$) minutes of superfusion. The compound under study is added to the superfusing medium 20 minutes prior to the second potassium stimulation. The residual radioactivity in the slices at the end of the experiment together with that in the superfusate fractions is measured by liquid scintillation counting using a dual label programme for tritium and carbon-14.

Calculations

The amount of radioactivity (either tritium or carbon-14) in each fraction is expressed as a percentage of the respective total radioactivity in the tissue at the start of the respective collection period. The amount of radioactivity released above basal by the increased potassium is calculated and the ratio S2/S1 obtained. The S2/S1 ratio from drug-treated slices is expressed as a percentage of the control S2/S1 ratio. For compounds achieving inhibition of 30% or more p$D_2$ values are calculated from plots of inhibition of release versus concentration of drug. Failure to inhibit the release of noradrenaline indicates that the molecule has no GABA$_B$ agonist activity.

RESULTS

In the aforementioned test the following representative compound gave the result shown:

| Compound | GABA autoreceptor Inhibition of release of GABA at 10$^{-5}$ M | Inhibition of release of noradrenaline at 10$^{-5}$ M |
|---|---|---|
| 3-[N,N-bis-(4-Chlorobenzyl)-amino]propylphosphonic acid | 17% | 17% |

In another aspect this invention provides use of a compound of formula I for the preparation of a medicament for the treatment of senile dementia and/or depression.

This invention also provides processes for preparing the compounds of the invention.

Compounds of formula I may be prepared by any one of the following processes:

a) alkylating a compound of formula II, IIa or IIb

Ar-A-NH-E            II

Ar-A-NH-B-D$^1$        IIa

E-NH-B-D$^1$           IIb wherein Ar, E and A are as defined above and $D^1$ is —P(O)($R^3$)(OR$^4$) where $R^3$ and $R^4$ are as defined above or —P(O)(OR$^5$)(OR$^6$) in which $R^5$ and $R^6$ independently represent loweralkyl or $C_7$–$C_{12}$aralkyl with an appropriate compound of formula III; IIIa or IIIb:

hal-B-D$^1$            (III)

E$^1$-hal              (IIIa)

Ar-A-hal (IIIb)

wherein $D^1$, B, Ar and A are as defined above, hal represents chlorine or bromine, and $E^1$ is E is defined above excepting hydrogen, to give a compound of formula I wherein $R^1$ and $R^2$ indpendently represent lower alkyl or $C_7$–$C_{12}$ aralkyl or $R^3$ and $R^4$ are as defined above; or b) carrying out a reductive alkylation of a compound of formula II, IIa or IIb as defined above using an appropriate compound of formula IV, IVa or IVb

OHC-$B^1$-$D^1$ (IV)

OHC-$E^2$ (IVa)

OHC-$A^2$-Ar (IVb)

wherein $D^1$ is as defined above, $E^2$ is alkyl of 1 to 5 carbon atoms or $Ar^1$—$CH_2$— wherein $Ar^1$ is as defined above, $A^2$ is $CH_2$ and $B^1$ is an alkylene chain of 2 or 3 carbon atoms optionally substituted by lower alkyl, in the presence of a reducing agent such as sodium cyanoborohydride to give a corresponding compound of formula I wherein $R^1$ and $R^2$ independently represent lower alkyl or $C_7$–$C_{12}$ aralkyl or $R^3$ and $R^4$ are as defined above; or (c) reducing a compound of formula (V)

$$Ar-A-N-B-D^1 \atop R^7-CO$$ (V)

wherein $D^1$ is as defined above, $R^7$ is alkyl of 1 to 5 carbon atoms or $Ar^1$-$A^2$-; Ar, $Ar^1$, A and B are as defined above, and $A^2$ represents a direct bond or alkylene of 1 carbon atom optionally substituted by lower alkyl and/or an optionally substituted Ar group wherein Ar is as defined above, to give a corresponding compound of formula I as defined above wherein $R^1$ and $R^2$ independently represent lower alkyl or $C_7$–$C_{12}$ aralkyl and E is $R^7CH_2$ wherein $R^7$ is as defined above; or (d) reducing a compound of formula (VI)

$$Ar-A-N-CO-B^1-D^1 \atop E$$ (VI)

wherein Ar, A and E are as defined above, $D^1$ is as defined above and $B^1$ is as defined in connection with formula IV to give a corresponding compound of formula I wherein B is —$CH_2B^1$— or e) reacting a compound of formula

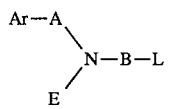 (VII)

wherein Ar,- A, B and E are as defined above and L represents a leaving group, e.g. a halogen such as chlorine or bromine, or an organic sulphonyloxy group such as an alkyl or aryl-sulphonyloxy group, e.g. methane- or toluene-sulphonyloxy, with a compound of formula:

(i) P(OR)$_3$ (VIII)

wherein R is lower alkyl or $C_7$–$C_{12}$ aralkyl, or (ii) $^\ominus$P(O)(OR$^5$)(OR$^6$) (IX)

(iii) $-\overset{O}{\overset{\|}{P}}(R^3)(OR^4)$ or (X)

wherein $R^3$, $R^4$, $R^5$ and $R^6$ are as defined above to give a corresponding compound of formula I, or f) converting an ester of formula I wherein D is —P(O)(O$R^1$)(O$R^2$) wherein at least one of $R^1$ and $R^2$ is lower alkyl or $C_7$–$C_{12}$ aralkyl, or —P(O) ($R^3$) (O$R^4$) to a corresponding compound of formula I wherein D is P(O)(O$R^1$)(O$R^2$) wherein $R^1$ and $R^2$ are both hydrogen or one is lower alkyl or $C_7$–$C_{12}$ aralkyl, or P(H)(=O)(OH), or g) reducing a compound of formula $$ArA^2CON-BD^1 \atop E$$ (XI)

wherein Ar, $A^2$, E, B and $D^1$ and as defined above, to give a corresponding compound of formula I wherein A is —$A^2CH_2$—.

With regard to process (a) the reaction may be conveniently carried out in the presence of an inert solvent and a base such as a tertiary amine (e.g. diisopropylethylamine) with heating if required. Examples of suitable inert solvents are dimethylformamide, acetonitrile and dimethylsulphoxide.

With regard to process (b) the reductive alkylation is conveniently carried out in an inert solvent, depending on the reducing agent, and without heating. When the reducing agent is sodium cyanoborohydride the solvent may be an aqueous alcohol such as aqueous ethanol. Catalytic hydrogenation may also be used. e.g. using Pd/C and an alcohol solvent, eg. ethanol.

Process (c), (d) and (g) may be carried out using a $P_2S_5$ and Raney nickel reduction. Process e) (i) may be carried out under conditions suitable for the Arbuzov reaction. With regard to process e) (ii) and process e) (iii) the anion of the compounds of formulae IX and X may be generated using sodium hydride. Process (f) may be carried out by complete or partial hydrolysis (using acid or base catalysis); ester cleavage (e.g. using trimethyl silylbromide or iodide) or hydrogenation (to remove $R^1$ and/or $R^2$ when benzyl, e.g. using Pd/C).

The starting materials of formula II used in process (a) are known compounds or can be prepared by analogous methods e.g. by reducing an amide of formula Ar-A-NHCO-$E^1$ where $E^1$ has one $CH_2$ group less than E. Compounds of formula V can be prepared by acylating a corresponding compound of formula Ar-A-NH-B-$D^1$ using an acid chloride of formula $R^7$ COCl. Compounds of formula Ar-A-NH-B-$D^1$ can themselves be prepared by alkylating amines of formula $NH_2$-B-$D^1$ using a halide of formula Ar-A-hal.

Compounds of formula XI can be prepared by acylating an amine of formula HN(E)B$D^1$ using an acid chloride of formula Ar$A^2$COCl.

Compounds of formula VI can be prepared by acylating amines of formula Ar-A-NH-E using an acid chloride of formula ClCO.$B^1$-$D^1$ wherein $B^1$ has the value defined in connection with process (d).

Starting materials for the processes described herein are known compounds or can be prepared by analogous methods for known compounds.

In any of the aforementioned reactions compounds of formula I may be isolated in free base form or as acid addition salts as desired. Examples of such salts include salts with pharmaceutically acceptable acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or tosylic acid.

When acidic substituents are present it is also possible to form salts with strong bases, e.g. those of alkali metals (such as sodium or potassium). Such salts of the compounds of formula I are included within the scope of this invention.

This invention also provides pharmaceutical compositions comprising a compound of formula I or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient. (with or without other carrier) is surrounded by carriers, which is thus in association with it. Similarly cachets are included. Sterile liquid form compositions include sterile solutions, suspensions, emulsions, syrups, and elixirs.

The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g. 25 mg to 250 mg, according to the particular need and activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound.

Compounds of formula I wherein at least one of $R^1$ and $R^2$ are lower alkyl or aralkyl, or $R^3$ and $R^4$ are as defined above are intermediates to compounds of formula I wherein D is $-PO_3H_2$ or $-PO_2H_2$.

The following Examples illustrate the invention and methods for preparing compounds of the invention.

EXAMPLE 1

3-[N,N-bis-(4-chlorobenzyl)amino]propylphosphonic acid diethyl ester a) 3-[N,N-bis-(4-chlorobenzyl)amino]propyl chloride was prepared by halogenating 3-[N,N-bis-(4-chlorobenzyl)amino]propanol using thionyl chloride.

b) 3-[N,N-bis-(4-chlorobenzyl)amino]propyl chloride (1.8 g 0.0054 moles) was dissolved in diethyl phosphlte (10 ml, large excess). Sodium hydride (2 g, excess) was added, then the mixture heated to 160° C. for 18 hours. After cooling the mixture was taken up into brine (50 ml) and the product extracted into chloroform (3×50 ml), then dried ($MgSO_4$). Excess triethyl phosphate was distilled out of the mixture at 150° C., 20 mmHg to give the title compound (1.7 g). infra red (liquid) strong broad bonds at 1241, 1090, 1050, 1020 and 965 $cm^{-1}$.

EXAMPLE 2

3-[N,N-bis-(4-Chlorobenzyl)amino]propyl phosphonic acid

3-[N,N-bis-(4-chlorobenzyl)amino]propyl phosphonic acid diethyl ester (prepared according to Example 1) was dissolved in 8N HCl (25 ml), then a small amount of isopropyl alcohol added to effect solution. After heating for 6 hours, evaporation gave the title compound as a glass.

Infra red (nujol mull): Sharp peaks at 1090 and 1016 $cm^{-1}$ on a background in 900–1250 $cm^{-1}$ region.

This was purified by crystallisation from hot water to give the dihydrate of the title compound, top. 161°–165° C.

$C_{17}H_{20}Cl_2NO_3$ $P.2H_2O$ requires: C,48.1; H,5.7: N,3.3% Found : C,48.0; H,5.9; N,3.2%

EXAMPLES 3–5

In a similar manner to Examples 1 and 2 the following phosphonous compounds of formula A prepared according to the reaction

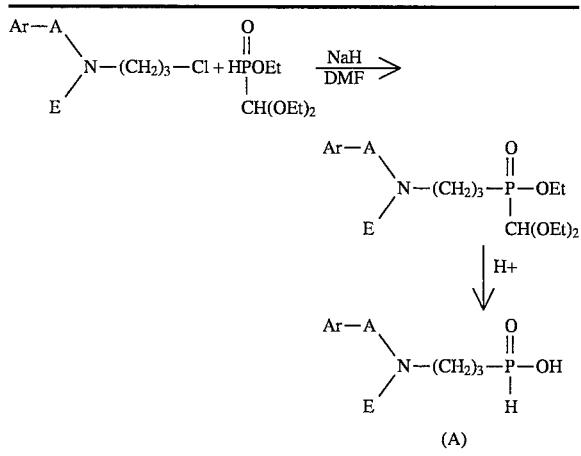

wherein:
Example No     Ar            A            E

-continued

| Ex No | Ar | A | E |
|---|---|---|---|
| 3 | 1-naphthyl | $CH_2$ | $CH_3$ |
| 4 | 4-chlorophenyl | $CH_2$ | $CH_3$ |
| 5 | 1-naphthyl | $CH_2$ | 1-naphthylmethyl |

EXAMPLES 6–8

In a similar manner to Examples 1 and 2 the following phosphonic compounds of formula B are prepared according to the reaction

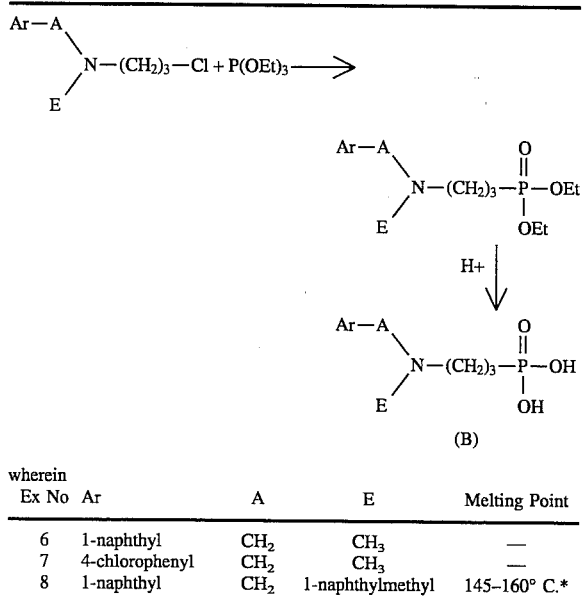

(B)

wherein

| Ex No | Ar | A | E | Melting Point |
|---|---|---|---|---|
| 6 | 1-naphthyl | $CH_2$ | $CH_3$ | — |
| 7 | 4-chlorophenyl | $CH_2$ | $CH_3$ | — |
| 8 | 1-naphthyl | $CH_2$ | 1-naphthylmethyl | 145–160° C.* |

*as the monohydrochloride, quarterhydrate salt

We claim:

1. A compound of formula

(I)

wherein E represents hydrogen, $C_1$–$C_6$ alkyl or a group $Ar^1$-$A^1$;

Ar and $Ar^1$ when present each, independently, represent an aryl group which is phenyl or naphthyl or a mono- or bi-cyclic heteroaryl group of 5 to 10 ring atoms wherein the heteroatoms are selected from oxygen, nitrogen and sulphur, which may be optionally substituted by one or more substituents selected from alkyl of 1 to 6 carbon atoms, alkoxy of 1 to 6 carbon atoms, halogen, haloalkyl of 1 to 6 carbon atoms, haloalkoxy of 1 to 6 carbon atoms, cyano, amino, mono- or di-($C_1$–$C_6$)alkylamino, hydroxy and nitro;

A and $A^1$ when present are the same or different alkylene groups having one or two carbons linking Ar or $Ar^1$ to N, each optionally substituted by alkyl of 1 to 6 carbon atoms or an optionally substituted Ar group as defined above, B is a straight chain alkylene group of 3 or 4 carbon atoms optionally substituted by alkyl of 1 to 6 carbon atoms, and D represents

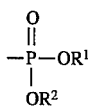

where $R^1$ and $R^2$ are independently hydrogen, alkyl of 1 to 6 carbon atoms or aralkyl of 7 to 12 carbon atoms;

with the proviso that, when B is a propylene group optionally substituted by one lower alkyl group, Ar-A- does not represent unsubstituted aralkyl.

2. A compound as claimed in claim 1 in which A and $A^1$ when present are independently a group of formula —$CHR^8$— where $R^8$ is hydrogen, alkyl of 1 to 4 carbon atoms or a phenyl, naphthyl, or mono- or bi-cyclic heteroaryl group in which the heteroatoms are selected from oxygen, nitrogen and sulphur, said group optionally substituted as defined for aryl or heteroaryl in claim 1.

3. A compound as claimed in claim 2 in which the optional substituents on the Ar, $Ar^1$ or $R^8$ group are independently selected from one or more of the following: methyl, ethyl, propyl, butyl, methoxy, ethoxy, n-propoxy, n-butoxy, fluorine, chlorine, bromine, chloromethyl, chloroethyl, trifluoromethyl, hydroxy, trifluoromethoxy, cyano, amino, methylamino, ethylamino, n-propylamino, dimethylamino, diethylamino, methylethylamino and nitro.

4. A compound as claimed in claim 1 wherein B is —$(CH_2)_3$-optionally substituted by methyl.

5. A compound as claimed in claim 1 wherein $R^1$ and $R^2$ are the same or different and each represent hydrogen, methyl, ethyl, propyl, butyl, benzyl or 2-phenethyl.

6. A compound as claimed in claim 1 when in the form of
   (a) a salt of an acid selected from hydrochloric, hydrobromic, hydroiodic, sulphuric, phosphoric, nitric, acetic, citric, tartaric, fumaric, succinic, malonic, formic, maleic, methanesulphonic and tosylic acid, or
   (b) when an acidic group is present, the sodium or potassium salt.

7. 3-[N,N-bis-(4-Chlorobenzyl)amino]proplphosphonic acid diethyl ester.

8. 3-[N,N-bis-(4-Chlorobenzyl)amino]propylphosphonic acid.

9. A pharmaceutical composition comprising a compound of formula I as defined in claim 1 or a pharmaceutically acceptable salt thereof and a pharmaceutically acceptable carrier.

10. A method of treating depression or memory impairment disorders or dementias in a mammal so afflicted, comprising administering to said mammal an amount effective to alleviate depression or memory impairment or dementia of a compound of formula

(I)

wherein E represents hydrogen, $C_1$–$C_6$ alkyl or a group $Ar^1$-$A^1$;

Ar and $Ar^1$ when present each, independently, represent an aryl group which is phenyl or naphthyl or a mono- or bi-cyclic heteroaryl group of 5 to 10 ring atoms wherein the heteroatoms are selected from oxygen, nitrogen and sulphur, which may be optionally substituted by one or more substituents selected from alkyl of 1 to 6 carbon atoms, alkoxy of 1 to 6 carbon atoms, halogen, haloalkyl of 1 to 6 carbon atoms, haloalkoxy of 1 to 6 carbon atoms, cyano, amino, mono- or di-$(C_1-C_6)$alkylamino, hydroxy and nitro;

A and $A^1$ when present are the same or different alkylene groups having one or two carbons linking Ar or $Ar^1$ to N, each optionally substituted by alkyl of 1 to 6 carbon atoms or an optionally substituted Ar group as defined above, B is a straight chain alkylene group of 3 or 4 carbon atoms optionally substituted by alkyl of 1 to 6 carbon atoms, and D represents

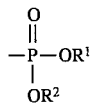

where $R^1$ and $R^2$ are independently hydrogen, alkyl of 1 to 6 carbon atoms or aralkyl of 7 to 12 carbon atoms;

or a pharmaceutically acceptable salt thereof, with the proviso that, when B is a propylene group optionally substituted by one lower alkyl group, Ar-A- does not represent unsubstituted aralkyl.

11. A method of treating depression or memory impairment disorders or dementias wherein Ar-A- and $Ar^1$-$A^1$- of the compound of formula I as claimed in claim 10 are the same.

12. A method of treating depression or memory impairment disorders or dementias wherein the compound of formula I as claimed in claim 10 is in the form of (a) a salt of an acid selected from hydrochloric, hydrobromic, hydroiodic, sulphuric, phosphoric, nitric, acetic, citric, tartaric, fumaric, succinic, malonic, formic, maleic, methanesulphonic and tosylic acid, or (b) when an acidic group is present, the sodium or potassium salt.

13. A method of treating depression or memory impairment disorders or dementias wherein the compound of formula I as claimed in claim 10 is 3-{N,N-bis-(4-chlorobenzyl)amino)propyl phosphonic acid or the diethyl ester thereof.

\* \* \* \* \*